United States Patent [19]

Herbert

[11] Patent Number: 4,680,273

[45] Date of Patent: Jul. 14, 1987

[54] ASSAY FOR VITAMIN B12 DEFICIENCY

[76] Inventor: Victor Herbert, 322 E. 61st St., New York, N.Y. 10021

[21] Appl. No.: 865,846

[22] Filed: May 22, 1986

Related U.S. Application Data

[63] Continuation-in-part of Ser. No. 760,100, Jul. 29, 1985, abandoned, which is a continuation-in-part of Ser. No. 713,834, Mar. 20, 1985, abandoned.

[51] Int. Cl.$^4$ ............................................. G01N 33/82
[52] U.S. Cl. ......................................... 436/92; 436/93; 436/96; 436/177; 436/178; 436/505; 436/811
[58] Field of Search ..................... 436/91, 92, 93, 96, 436/103, 104, 106, 109, 111, 127, 128, 131, 174, 175, 177, 178, 505, 811, 825

[56] References Cited

U.S. PATENT DOCUMENTS

| | | | |
|---|---|---|---|
| 4,167,556 | 9/1979 | Selhub et al. | 436/505 |
| 4,188,189 | 2/1980 | Allen | 436/825 X |
| 4,273,757 | 6/1981 | Selhub et al. | 436/505 |
| 4,300,907 | 11/1981 | Mansbach et al. | 436/505 |
| 4,333,918 | 6/1982 | Carney et al. | 436/505 |
| 4,351,822 | 9/1982 | Allen | 436/505 X |
| 4,418,151 | 11/1983 | Forand et al. | 436/505 |
| 4,426,455 | 1/1984 | Tovey et al. | 436/825 X |
| 4,451,571 | 5/1984 | Allen | 436/505 |

FOREIGN PATENT DOCUMENTS 8001415 7/1980 PCT Int'l Appl. ................. 436/505

OTHER PUBLICATIONS

Kolhouse et al, New England Journal of Medicine, vol. 299, No. 15, pp. 785-792, 1978.
Allen et al, J. of Bio. Chem., vol. 248, No. 10, pp. 3660-3669, 1973.
Frenkel et al, Am. J. of Clin. Path., vol. 53, No. 6, pp. 891-903, 1970.

*Primary Examiner*—Barry S. Richman
*Assistant Examiner*—Robert J. Hill, Jr.
*Attorney, Agent, or Firm*—Elliot M. Olstein

[57] ABSTRACT

An assay for Vitamin $B_{12}$ deficiency by determining for a blood sample that essentially all of the Vitamin $B_{12}$ is carried by a combination of TCI and TCIII and/or essentially no Vitamin $B_{12}$ is carried by TCII. TCII may be conveniently separated from a combination of TCI and TCIII by precipitating TCII with silica. Vitamin $B_{12}$ deficiency may be determined prior to the onset of anemia and/or nerve damage by determining a decrease in Vitamin $B_{12}$ carried by TCII.

16 Claims, No Drawings

ASSAY FOR VITAMIN B12 DEFICIENCY

This application is a Continuation-in-Part of U.S. patent application Ser. No. 760,100, filed on July 29, 1985, now abandoned, which is a Continuation-in-Part of U.S. patent application Ser. No. 713,834, filed on Mar. 20, 1985, now abandoned.

This invention relates to determining Vitamin $B_{12}$, and more particularly to a new and improved procedure for determining Vitamin $B_{12}$ deficiency.

In many cases, as an aid to diagnosing a deficiency in Vitamin $B_{12}$, a physician requests an assay for Vitamin $B_{12}$ in a patient's blood sample. In general, such assays are currently accomplished by a so-called competitive protein binding assay. In such an assay, Vitamin $B_{12}$ present in a blood sample and Vitamin $B_{12}$ labeled with an appropriate marker, such as a radioactive marker, compete for a limited number of binding sites on a binder for Vitamin $B_{12}$, in particular, a protein binder, such as intrinsic factor. The amount of tracer which becomes bound to the protein is inversely proportional to the amount of Vitamin $B_{12}$ in the sample. As a result, by determining the amount of Vitamin $B_{12}$ tracer in the bound and/or free fraction, and comparing such ascertained value with a standard curve prepared by effecting the assay with samples containing known quantities of Vitamin $B_{12}$, the amount of Vitamin $B_{12}$ in the sample can be determined. Such amount of Vitamin $B_{12}$ can then be compared with a range of expected values for Vitamin $B_{12}$ with respect to so-called "normal" Vitamin $B_{12}$ samples, and so-called "deficient" Vitamin $B_{12}$ samples so as to ascertain whether or not a particular patient's sample is deficient with respect to Vitamin $B_{12}$.

Although such assays are an effective tool for determining Vitamin $B_{12}$ deficiency, it is known that the assay sometimes provides "false negatives" (an indication of a lack of Vitamin $B_{12}$ deficiency when there is, in fact, Vitamin $B_{12}$ deficiency) and "false positives" (an indication that there is Vitamin $B_{12}$ deficiency when there is, in fact, no Vitamin $B_{12}$ deficiency).

Moreover, in most cases, such assays do not determine Vitamin $B_{12}$ deficiency until the onset of anemia, when in fact, a patient may be deficient in Vitamin $B_{12}$ before the onset of anemia.

As a result, there is a need for improvements in methods for determining Vitamin $B_{12}$ deficiency by a Vitamin $B_{12}$ assay procedure.

In accordance with one aspect of the present invention, there is provided a process for determining Vitamin $B_{12}$ deficiency wherein there is assayed in a blood sample the Vitamin $B_{12}$ carried by transcobalamin II and/or Vitamin $B_{12}$ present in the sample other than Vitamin $B_{12}$ which is carried by transcobalamin II (TCII) in particular, Vitamin $B_{12}$ carried by the combination of transcobalamin I (TC I) and transcobalamin III (TCIII), with Vitamin $B_{12}$ deficiency being determined by either the essential absence of transcobalamin II having bound Vitamin $B_{12}$ and/or essentially all of the Vitamin $B_{12}$ in the sample being Vitamin $B_{12}$ other than Vitamin $B_{12}$ carried by transcobalamin II.

More particularly, applicant has found that where there is Vitamin $B_{12}$ deficiency, essentially none of the Vitamin $B_{12}$ present in a blood sample is carried by transcobalamin II, whereby essentially all of the Vitamin $B_{12}$ present in the sample is carried by transcobalamin I and III. In the case where a patient is not deficient with respect to Vitamin $B_{12}$, then in a blood sample, Vitamin $B_{12}$ is carried by transcobalamin II, as well as the other transcobalamins, whereby essentially all of the Vitamin $B_{12}$ in the sample is not carried by the combination of transcobalamin I and transcobalamin III.

Applicant has also found that the amount of Vitamin $B_{12}$ carried by transcobalamin II is depleted prior to the onset of anemia whereby, by proceeding in accordance with the present invention, it is possible to determine the early stages of $B_{12}$ deficiency, prior to the onset of anemia; for example, the forms of $B_{12}$ deficiency where there is $B_{12}$ depletion (gradual loss of stored $B_{12}$) and/or $B_{12}$ deficient blood formation, prior to the onset of anemia. Accordingly, a falling in the amount of Vitamin $B_{12}$ carried by TCII is indicative of $B_{12}$ deficiency prior to anemia. Thus, by detecting a decrease in the amount of Vitamin $B_{12}$ carried by TCII, it is possible to detect a negative $B_{12}$ balance prior to essentially complete depletion of Vitamin $B_{12}$ carried by TCII and prior to onset of anemia.

In this manner, $B_{12}$ deficiency can be determined at early stages, whereby treatment can begin prior to the onset of anemia.

Applicant believes that determining whether or not TCII in serum has a falling amount of Vitamin $B_{12}$ bound thereto can be employed as an early indicator of loss of Vitamin $B_{12}$ in the tissues, which is an early indication of eventual anemia and/or nerve damage. In effect, when the TCII status of the serum shows a decrease in holo transcobalamin II (TCII containing bound Vitamin $B_{12}$) which produces an increase in apo transcobalamin II (TCII essentially free of bound Vitamin $B_{12}$), even though serum levels may be in the normal range of expected Vitamin $B_{12}$ values, in fact, the amount of Vitamin $B_{12}$ being transferred to tissues which require Vitamin $B_{12}$ is less than those tissues need to sustain a normal state of Vitamin $B_{12}$, whereby such tissues are going into negative $B_{12}$ balance (giving up more Vitamin $B_{12}$ than they are receiving). A decrease in holo TCII may be ascertained by comparison with a "normal range" for holo TCII levels or by comparing holo TCII levels of a patient over a period of time. Negative $B_{12}$ balance produces Vitamin $B_{12}$ depletion, and when depletion is sufficiently severe, anemia and nerve damage will develop. Accordingly, the determination of whether or not TCII contains decreasing amounts of Vitamin $B_{12}$ and, in particular, an essential absence of $B_{12}$, may be employed as a screening assay to ascertain, at an early stage, whether or not a patient is in negative $B_{12}$ balance which may eventually lead to anemia and/or nerve damage. In this manner, treatment for Vitamin $B_{12}$ deficiency can be initiated to prevent a asevere depletion of Vitamin $B_{12}$ which can lead to anemia and/or nerve damage.

As known in the art, in the plasma, Vitamin $B_{12}$ is bound to two main classes of serum proteins, with the first class being transcobalamin II, which moves electrophoretically with the beta globulins, and the second class being transcobalamin I and III, which are in the class of R binders, and move electrophoretically differently from transcobalamin II. Applicant has found that in the case where there is a Vitamin $B_{12}$ deficiency, essentially none of the Vitamin $B_{12}$ is carried by the transcobalamin II, and essentially all of the Vitamin $B_{12}$ is carried by the remaining serum binding proteins; i.e., transcobalamin I and III. As a result, a deficiency in Vitamin $B_{12}$ can be ascertained by determining the Vitamin $B_{12}$ which is carried by transcobalamin II and/or by determining that essentially all of the Vitamin $B_{12}$ is carried by transcobalamin I and III.

In accordance with an aspect of the present invention, the Vitamin $B_{12}$ which is carried by transcobalamin II may be determined by providing a sample which contains essentially only transcobalamin II (transcobalamin II has been separated from the other serum proteins) and determining the Vitamin $B_{12}$ content of such sample. Alternatively, there can be provided a blood sample which contains a combination of transcobalamin I and III, and the Vitamin $B_{12}$ content of such sample can then be determined and compared with Vitamin $B_{12}$ present in a blood sample which contains all three transcobalamins.

As a further alternative, the amount of Vitamin $B_{12}$ which is carried by transcobalamin II in a blood sample may be determined by selectively freeing only the Vitamin $B_{12}$ from the transcobalamin II, and determining such Vitamin $B_{12}$.

As still another alternative, the Vitamin $B_{12}$ which is carried by transcobalamin I and III may be determined by selectively freeing Vitamin $B_{12}$ from only the transcobalamin I and III of a blood sample, and determining such Vitamin $B_{12}$.

There are a wide variety of methods available for separating a blood sample into a first sample which contains TCI and TCIII, essentially free of TCII, and a second sample which contains TCII, essentially free of TCI and TCIII. As known in the art, TCI and TCIII are glycoproteins, whereas TCII is a polypeptide, and procedures for separating glycoproteins from polypeptides may also be employed for separating blood into separate samples containing a combination of TCI and TCIII, and a sample containing TCII.

In accordance with one procedure, which is preferred, TCII may be precipitated from a blood sample so as to provide a supernatant sample which contains TCI and TCIII, essentially free of TCII, and a precipitate of TCII, which is essentially free of TCI and TCII. Such precipitation of TCII may be accomplished by the use of a finely divided precipitated silica, such as the one sold under the mark Quso, sold by Philadelphia Quartz Corporation, and in particular, a silica sold under the marks Quso G-761 and Quso G-32. Although the use of silica is preferred, other methods for separating TCII from a sample are equally applicable.

In accordance with another procedure, it is possible to precipitate TCI and TCIII to provide a supernatant which contains TCII essentially free of TCI and TCIII, and a precipitate which contains TCI and TCIII, essentially free of TCII. Thus, for example, TCI and TCIII may be precipitated from blood by the use of lectins.

Another procedure for separating TCII from TCI and TCIII is by use of an antibody to TCII so as to selectively bind the TCII for separating the TCII from TCI and TCIII. Alternatively, an antibody for TCI and TCIII may be employed to selectively bind TCI and TCIII for separating TCI and TCIII from TCII. As still another alternative, lectins may be employed for separating TCI and TCIII from TCII in that lectins selectively bind glycoproteins. As still another alternative, antibody or lectin can be coupled to a solid support, to more easily separate TCII from TCI and TCIII. As a further alternative, at pH6, TCII binds to carboxymethylcellulose-sephadex, but TCI and III do not. The above methods and others should be apparent to those skilled in the art from the teachings herein.

As should be apparent, however, a preferred method is using a material, such as silica to selectively adsorb TCII in that silica is readily available, and can be easily used for effecting such separation. In such an embodiment, Vitamin $B_{12}$ deficiency or the lack thereof may then be readily determined by running a Vitamin $B_{12}$ assay on the sample portion containing the separated TCII, with the essential absence of Vitamin $B_{12}$ in said sample indicating a deficiency of Vitamin $B_{12}$, and with the presence of Vitamin $B_{12}$ in such a sample indicating that there is no deficiency in Vitamin $B_{12}$. For example, the precipitate of TCII on silica may be contacted with a solution of acetone in acetic acid to remove the TCII, including the Vitamin $B_{12}$ carried by the TCII, from the silica. The resulting solution may then be subjected to an assay for Vitamin $B_{12}$; e.g., a radioassay for Vitamin $B_{12}$, which includes removal of Vitamin $B_{12}$ from the transcobalamin II (for example, by heating), followed by contact with tracer and binder. Alternatively, hydrochloric acid at pH 2 will destroy the TCII and remove the $B_{12}$ for assay.

As hereinabove indicated, it is also possible to determine the Vitamin $B_{12}$ carried by TCII and/or the Vitamin $B_{12}$ carried by a combination of TCI and TCIII in a blood sample by selectively freeing Vitamin $B_{12}$ from TCII and/or a combination of TCI and TCIII. In such a case, it is not necessary to effect a sepatation of TCII from a combination of TCI and TCIII in that the Vitamin $B_{12}$ carried by the respective proteins is selectively freed for determination by an appropriate assay.

Thus, for example, it is possible to selectively free Vitamin $B_{12}$ from TCII, while maintaining Vitamin $B_{12}$ bound to TCI and TCIII by an appropriate change in the pH and ionic strength of the sample. Vitamin $B_{12}$ dissociates from TCII when both ionic strength and pH are low (Stenman, Scand. J. Haem. 13:129-134, 1974).

After selectively freeing the Vitamin $B_{12}$ from the TCII, the Vitamin $B_{12}$ content can be determined, with essential absence of Vitamin $B_{12}$ indicating a Vitamin $B_{12}$ deficiency, and the presence of Vitamin $B_{12}$ indicating that there is no Vitamin $B_{12}$ deficiency.

The assay which is employed for determining Vitamin $B_{12}$ carried by TCII in a blood sample and/or Vitamin $B_{12}$ carried by a combination of TCI and TCIII in a blood sample may be any one of a wide variety of assays which are available for determining Vitamin $B_{12}$. Applicant has found that it is not necessary to limit the Vitamin $B_{12}$ assay to an assay for only cobalamins in that in the case where a patient is deficient in Vitamin $B_{12}$, transcobalamin II is essentially free of all corrinoids. Thus, the Vitamin $B_{12}$ assay for determining Vitamin $B_{12}$ carried by TCII and/or Vitamin $B_{12}$ carried by a combination of TCI and TCIII need not be specific for cobalamins; i.e., the assay may either be specific for cobalamins, or be an assay for total corrinoids.

Thus, for example, in a competitive protein binding type of assay, the binder used in the assay may be specific for cobalamin (intrinsic factor), or may be a binder for total corrinoids (R-protein or a mixture of intrinsic factor and R-protein).

The assay for determining Vitamin $B_{12}$ is preferably effected by a competitive protein binding or immunoassay procedure. It is to be understood, however, that other procedures for determining Vitamin $B_{12}$ in a blood sample may also be employed; for example, a microbiological assay.

For example, in a competitive protein binding assay or immunoassay, the blood sample which contains TCII, essentially free of TCI and TCIII, or the blood sample which contains TCI and TCIII, essentially free of TCII, is initially treated to release Vitamin $B_{12}$ from the serum proteins; i.e., as appropriate, TCII or a combination of TCI and TCIII. Such release may be accomplished by any one of a wide variety of procedures, including, boiling of the sample, or by use of the so-called "no boil" procedures. The assay for Vitamin $B_{12}$ in the sample may then be accomplished by the use of an appropriate binder, which binder, as hereinabove noted, may be a binder which is specific for cobalamins, or which may be a binder for all corrinoids. In a competitive protein binding assay, the binder is a protein type of binder, such as intrinsic factor, R-protein, etc. In an immunoassay, the binder is an appropriate antibody, which may be a monoclonal antibody, or a polyclonal antibody. The assay is accomplished by use of a tracer, which is either Vitamin $B_{12}$ or an appropriate analog thereof labeled with a detectable marker. The term "appropriate analog" means that the analog of Vitamin $B_{12}$ is also bound by the $B_{12}$ binder used in the assay. The marker is generally a radioactive marker such as radioactive cobalt; however, it is to be understood that the marker could be a radioactive marker other than radioactive cobalt, such as radioactive iodine, or may be another marker, such as a dye (fluorescent and/or absorbing dye), enzyme, etc. In the assay, the tracer and any Vitamin $B_{12}$ present in the sample being assayed compete for a limited number of binding sites on the binder, and the amount of tracer which becomes bound to the binder is inversely proportional to the amount of Vitamin $B_{12}$ in the sample. The binder may be employed in either supported or unsupported form. In the case where the binder is supported on a solid support, the bound and free fractions may be separated without the use of a separating agent. In the case where the binder is employed in an unsupported form, then the bound and free fractions may be separated by the use of an appropriate separating agent, such as coated charcoal, or other adsorbent.

The amount of Vitamin $B_{12}$ in the sample may then be determined by comparing the results with an assay performed with known quantities of Vitamin $B_{12}$. Thus, for example, in the case where the sample contains TCII essentially free of TCI and TCIII, the assay results may be compared with assay results for a sample which was known to contain essentially no Vitamin $B_{12}$ so as to determine whether or not the sample being assayed contains any Vitamin $B_{12}$.

The procedures for effecting a determination of Vitamin $B_{12}$ in a sample are generally known in the art, and no further details in this respect are deemed necessary for a complete understanding of the present invention.

The procedure of the present invention may be effectively employed in conjunction with an assay for Vitamin $B_{12}$ on a blood sample which determines the Vitamin $B_{12}$ carried by the serum proteins; i.e., TCI, TCII, and TCIII. Thus, for example, in accordance with an aspect of the present invention, the assay is effected on a patient's sample to determine Vitamin $B_{12}$ in the sample without separating TCI and/or TCII and/or TCIII from the sample and the assayed Vitamin $B_{12}$ is compared with a range of expected values for the assay.

The assay is then repeated to determine in the patient's sample the Vitamin $B_{12}$ carried by the TCII and/or the combination of TCI and TCIII. If essentially none of the Vitamin $B_{12}$ in the patient's sample is carried by TCII and/or essentially all of the Vitamin $B_{12}$ in the patient's sample is carried by the combination of TCI and TCIII, then irrespective of the assay results, with respect to purported Vitamin $B_{12}$ deficiency in the patient's sample containing TCI, TCII and TCIII, such patient is deficient in Vitamin $B_{12}$.

Similarly, if a portion of the Vitamin $B_{12}$ of the patient's sample is carried by the TCII; i.e., TCI and TCIII do not carry essentially all of the Vitamin $B_{12}$ present in the patient's sample, then irrespective of the assay results with respect to Vitamin $B_{12}$ deficiency obtained from an assay of the patient's sample containing TCI, TCII and TCIII, such patient is not deficient with respect to Vitamin $B_{12}$. As should be apparent, in this manner, "false positives" and/or "false negatives" in a Vitamin $B_{12}$ assay can be essentially eliminated.

Although in a preferred aspect, the present invention is employed in conjunction with an assay of the patient's sample which contains TCI, TCII and TCIII, it is to be understood that it would be possible to effect a determination of Vitamin $B_{12}$ deficiency by assaying for Vitamin $B_{12}$ carried by transcobalamin II without determining the Vitamin $B_{12}$ level in a sample containing TCI, TCII, and TCIII. If there is essentially no Vitamin $B_{12}$ carried by the TCII, then the patient is deficient with respect to Vitamin $B_{12}$. Similarly, if the TCII carries Vitamin $B_{12}$, then the patient is not deficient in Vitamin $B_{12}$.

As should be apparent, in the case where the Vitamin $B_{12}$ which is carried by TCI and TCIII is determined, it is not possible to ascertain whether essentially all of the Vitamin $B_{12}$ present in a patient's sample is carried by a coxbination of TCI and TCIII without also doing an assay on a portion of the patient's sample which contains TCI, TCII and TCIII.

In the present specification and claims, when it is stated that essentially none of the Vitamin $B_{12}$ (corrinoids and/or cobalamin) in a sample is carried by TCII or that there is an essential absence of Vitamin $B_{12}$ carried by TCII, it is meant that less than 30 pg and most generally less than 15 pg of the Vitamin $B_{12}$ present in 1 ml of the serum or plasma sample is carried by TCII, or stated in the alternative, all but 30 pg or less and most generally all but 15 pg or less of the Vitamin $B_{12}$ present in 1 ml of a patient's sample is carried by a combination of TCI and TCIII.

In accordance with another aspect of the present invention, there is provided a reagent kit or package for performing a $B_{12}$ assay which includes in suitable reagent containers or vials, a binder for Vitamin $B_{12}$, a tracer for Vitamin $B_{12}$ and an adsorbent or precipitant for transcobalamin II, such as precipitated silica. The tracer and the binder may be of the type hereinabove described. The tracer and/or binder may be included in the vial alone or in combination with another tracer and binder, respectively; for example, a folate binder and folate tracer, respectively, for use in simultaneous assay for Vitamin $B_{12}$ and folate.

The present invention will be further described with respect to the following example; however, the scope of the invention is not to be limited thereby.

EXAMPLE

An aliquot of 0.1 ml of the blood serum under study is placed in each of 2 conical-bottom test tubes labeled #1 and #2, each containing 1 ml of saline solution (0.9M). To test tube #2 is added 3 mg of precipitated silica (Quso G-671 - P-Q Corporation, Valley Forge, Pa.). Each test tube is then mixed on a Vortex for 3 seconds, centrifuged at 1500 g for 10 minutes, and the supernatant poured into another test tube and assayed for Vitamin $B_{12}$ content. The precipitate which remains in test tube #2 is mixd with 0.5 ml 20% acetone in 1% acetic acid and the tube is mixed on a Vortex for ten seconds to remove the adsorbed TCII, carrying Vitamin $B_{12}$ from the Quso. In the alternative, the precipitate which remains in test tube #2 is mixed with hydrochloride acid at pH 2 to destroy the TCII and free the Vitamin $B_{12}$ into the acid. After centrifugation at 1500g for 10 minutes, the supernatant is poured into test tube #3 and assayed for Vitamin $B_{12}$. The Vitaxin $B_{12}$ content of test tube #1 is the Vitamin $B_{12}$ carried by TC (I+II+III), the Vitamin $B_{12}$ content of the supernatant of test tube #2 is the Vitamin $B_{12}$ carried by TC (I +III) and the Vitamin $B_{12}$ content of the supernatant poured into test tube #3 is the Vitamin $B_{12}$ carried by TCII. Vitamin $B_{12}$ may be determined by the method of Lau et al Blood Vol. 26, pages 202-214 (1965).

Each of the Vitamin $B_{12}$ assays was effected by a radioassay in accordance with the protocol included in the Kolhouse, et al article, New England Journal of Medicine 299:785-92 (1978). The assay for total corrinoids (T Cor) used R- binder and the assay for cobalamin (cbl) used purified intrinsic factor. Test tube #1 and #2 contained 0.1 ml of serum and TCII was extracted from test tube #2 for use in test tube #3 with 3 mg of silica (quoso G-32) as hereinabove described. The results of the assays are included in the following table:

TABLE I

|   | Test Tube #1 TC(I, II & III) | | Test Tube #2 TC(I & III) | | Test Tube #3 TC(II) | |
|---|---|---|---|---|---|---|
|   | T Cor. | cbl | T Cor. | cbl | T Cor. | cbl |
| Six Normal Individuals | | | | | | |
| #1 | 540 | 340 | 482 | 259 | 53 | 70 |
| #2 | 761 | 612 | 584 | 503 | 165 | 101 |
| #3 | 711 | 470 | 674 | 411 | 32 | 55 |
| #4 | 467 | 240 | 417 | 161 | 50 | 51 |
| #5 | 630 | 435 | 561 | 375 | 61 | 60 |
| #6 | 581 | 354 | 508 | 294 | 68 | 66 |
| Five $B_{12}$ Deficient Patients | | | | | | |
| #1 | 134 | 85 | 135 | 82 | 0 | 0 |
| #2 | 47 | 54 | 63 | 46 | 0 | 0 |
| #3 | 250 | 30 | 259 | 31 | 0 | 0 |
| #4 | 177 | 47 | 195 | 36 | 0 | 0 |
| #5 | 276 | 63 | 271 | 64 | 0 | 0 |

The present invention is particularly advantageous in that it is possible to determine Vitamin $B_{12}$ deficiency in a patient's sample in a more accurate and reliable manner. Thus, by proceeding in accordance with the present invention, it is possible to determine Vitamin $B_{12}$ deficiency by determining Vitamin $B_{12}$ carried by TCII or a combination of TCI and TCIII in a sample. It has been found that such an assay will reduce or eliminate the "false positives" and/or "false negatives" inherent in a $B_{12}$ assay.

Moreover, unlike the assays which determine total Vitamin $B_{12}$ in the serum, by proceeding in accordance with the present invention, it is possible to determine Vitamin $B_{12}$ deficiency prior to the onset of anemia; e.g., Vitamin $B_{12}$ depletion and/or $B_{12}$ deficient blood formation.

Although the present invention is not limited to by any explanation, it is believed that at the onset of Vitamin $B_{12}$ deficiency, there is a depletion in the Vitamin $B_{12}$ carried by TC II, with the later stages of the deficiency being evidenced by a depletion of the amount of Vitamin $B_{12}$ carried by TC I and TC III. Since the major portion of Vitamin $B_{12}$ is carried by TC I and III in the early stages of deficiency, the total amount of Vitamin $B_{12}$ may be in the "normal range" of expected values; however, essentially all of such Vitamin $B_{12}$ is carried by TC I and TC III. It is only at the later stages of $B_{12}$ deficiency that the total amount of Vitamin $B_{12}$ in the serum is depleted to below the "normal range" of expected values, at which time, in most cases, there is an onset of anemia and/or nerve damage. Accordingly, by proceeding in accordance with the present invention, it is possible to determine and treat Vitamin $B_{12}$ deficiency before the onset of anemia and/or nerve damage.

Although the assay is described in terms of determining Vitamin $B_{12}$ carried by TCII, it is to be understood that such term encompasses determining whether TCII in the sample does or does not carry Vitamin $B_{12}$; i.e., whether or not TCII in the sample does or does not contain decreasing amounts of bound Vitamin $B_{12}$. As hereinabove described, if it is determined that the TCII in the sample has essentially no bound Vitamin $B_{12}$, such absence indicates a deficiency in Vitamin $B_{12}$. Similarly, if the TCII in the sample contains bound Vitamin $B_{12}$, such presence indicates a lack of deficiency in Vitamin $B_{12}$.

It is to be understood that when the terminology "determining Vitamin $B_{12}$ deficiency" is employed herein, it means determining that the patient is either deficient or lacks deficiency with respect to Vitamin $B_{12}$.

It is also to be understood that although it is believed that the Vitamin $B_{12}$ binding proteins in blood are comprised of TCI, TCII and TCIII, the scope of the present invention is not limited in this respect in that, as should be apparent, the invention would also be useful if serum binding proteins, in addition to such transcobalamins, are present in blood.

Numerous modifications and variations of the present invention are possible in light of the above teachings and, therefore, within the scope of the appended claims, the invention may be practiced otherwise than as particularly described.

What is claimed is:

1. A process for determining Vitamin $B_{12}$ deficiency, comprising:
    assaying in a blood sample at least one of (a) Vitamin $B_{12}$ carried by TCII and (b) Vitamin $B_{12}$ in the sample other than Vitamin $B_{12}$ carried by TCII; and determining Vitamin $B_{12}$ deficiency by at least one of (c) essential absence of Vitamin $B_{12}$ carried by TCII in the blood smaple and (d) essentially all Vitamin $B_{12}$ in the blood sample being Vitamin $B_{12}$ other than Vitamin $B_{12}$ carried by TCII.

2. The process of claim 1 wherein Vitamin $B_{12}$ is assayed by assaying for total corrinoids.

3. The process of claim 1 wherein Vitamin $B_{12}$ is assayed by assaying cobalamins.

4. The process of claim 1 wherein Vitamin $B_{12}$ is assayed by a radioassay.

5. The process of claim 1 wherein the blood sample is treated to separate TCII from the sample and Vitamin $B_{12}$ carried by the separated TCII is assayed to determine Vitamin $B_{12}$ deficiency.

6. The process of claim 5 wherein TCII is separated from the blood sample by precipitating TCII.

7. The process of claim 6 wherein TCII is precipitated with silica.

8. A process for determining Vitamin $B_{12}$ deficiency comprising:

assaying Vitamin $B_{12}$ derived from a first portion of a blood sample containing transcobalamin I, II, and III; comparing Vitamin $B_{12}$ assayed in the first portion with Vitamin $B_{12}$ assayed in at least a second portion of the blood sample, said second portion being at least one of a sample containing TCII essentially free of TCI and III, and a sample containing TCI and III essentially free of TCII; and determining Vitamin $B_{12}$ deficiency by at least one of (a) essentially all Vitamin $B_{12}$ assayed in the first portion being present in a second sample portion essentially free of TCII and (b) essentially no Vitamin $B_{12}$ assayed in the first portion being present in a second sample portion essentially free of TCI and III.

9. The process of claim 8 wherein Vitamin $B_{12}$ deficiency is determined by comparison of Vitamin $B_{12}$ in a second sample portion essentially free of TCI and III with Vitamin $B_{12}$ in the first sample portion containing TCI, II and III.

10. The process of claim 9 wherein the second sample portion is obtained by precipitating and recovering TCII or its bound Vitamin $B_{12}$ from a portion of the blood sample.

11. The process of claim 10 wherein TCII is precipitated with silica.

12. A process for screening a patient for Vitamin $B_{12}$ deficiency, comprising:

assaying TCII having Vitamin $B_{12}$ bound thereto in a blood sample of a patient; and determining Vitamin $B_{12}$ deficiency by a decrease in the amount of TCII having Vitamin $B_{12}$ bound thereto.

13. The process of claim 12 wherein a decrease in the amount of TCII having Vitamin $B_{12}$ bound thereto is measured by an essential absence of TCII having Vitamin $B_{12}$ bound thereto.

14. The process of claim 13 wherein TCII having Vitamin $B_{12}$ bound thereto is assayed by determining Vitamin $B_{12}$ in a blood sample portion containing TCII essentially free of TCI and TCIII.

15. The process of claim 13 wherein TCII having Vitamin $B_{12}$ bound thereto is assayed by assaying total corrinoids bound to TCII.

16. The process of claim 13 wherein TCII having Vitamin $B_{12}$ bound thereto is assayed by assaying for cobalamins bound to TCII.

* * * * *